United States Patent [19]

Griffiths

[11] Patent Number: 5,062,831
[45] Date of Patent: * Nov. 5, 1991

[54] CATHETER FOR USE IN THE SURGICAL CORRECTION OF A NASOLACRIMAL DUCT OBSTRUCTION

[76] Inventor: John D. Griffiths, 1738 S. 85th St., Omaha, Nebr. 68124

[*] Notice: The portion of the term of this patent subsequent to May 1, 2007 has been disclaimed.

[21] Appl. No.: 510,429

[22] Filed: Apr. 18, 1990

Related U.S. Application Data

[63] Continuation-in-part of Ser. No. 250,164, Sep. 28, 1988.

[51] Int. Cl.[5] .............................. A61M 25/00
[52] U.S. Cl. .................... 604/104; 604/280; 604/191
[58] Field of Search ............... 604/93, 104, 106, 264, 604/266, 268, 280, 8; 606/191, 196, 198, 108, 109

[56] References Cited

U.S. PATENT DOCUMENTS

| | | | |
|---|---|---|---|
| 3,726,284 | 4/1973 | Parker | 604/104 |
| 3,807,409 | 4/1974 | Paparella et al. | 604/264 |
| 3,976,081 | 8/1976 | Lapidot | 604/266 |
| 4,490,138 | 12/1984 | Lipsky et al. | 604/40 |
| 4,500,313 | 2/1985 | Young | 604/280 |
| 4,680,029 | 7/1987 | Ranford et al. | 604/280 |
| 4,695,275 | 9/1987 | Bruce et al. | 604/264 |
| 4,921,485 | 5/1990 | Griffiths | 604/104 |
| 4,973,301 | 11/1990 | Nissenkorn | 604/93 |

OTHER PUBLICATIONS

Lacrimal Drainage Surgery by James A. Katowitz.

Primary Examiner—C. Fred Rosenbaum
Assistant Examiner—Chalin Smith
Attorney, Agent, or Firm—Zarley, KcKee, Thomte, Voorhees & Sease

[57] ABSTRACT

A catheter for use in the surgical correction of a nasolacrimal duct obstruction comprising an elongated shank portion having a enlarged portions at the upper and lower ends thereof. When the catheter is properly placed during the surgical procedure, the enlarged portions of the catheter prevent longitudinal displacement thereof and prevents the "scarring over" of the nasolacrimal duct.

3 Claims, 1 Drawing Sheet

CATHETER FOR USE IN THE SURGICAL CORRECTION OF A NASOLACRIMAL DUCT OBSTRUCTION

CROSS-REFERENCE TO RELATED APPLICATION

This is a continuation-in-part application of Ser. No. 250,164 filed Sept. 28, 1988, now U.S. Pat. No. 4,921,485 issued May 1, 1990.

BACKGROUND OF THE INVENTION

This invention relates to a catheter and more particularly to a catheter which is used to improve the success of surgically correcting a nasolacrimal duct obstruction.

It is frequently necessary to correct, by way of surgery, a nasolacrimal duct obstruction. One method of correcting a nasolacrimal duct obstruction is through the silastic intubation of the nasolacrimal duct. In such a procedure, the free ends of a silastic tube are inserted downwardly into, and through, the puncta, canaliculi, nasolacrimal sac and nasolacrimal duct with the lower ends of the silastic tubing being positioned within the nose (inferior meatus) below the lower end of the nasolacrimal duct. The ends of the silastic tubing are normally cut so they do not protrude below the lower end of the patient's nose. The purpose of the silastic tubing is to provide a flow path for the tears to drain downwardly through the system around the exterior surface of the tubing.

One method of fixation of the silastic tubing is through the use of a rubber catheter which embraces the silastic tubing from the nasolacrimal sac to the lower end of the nasolacrimal duct. Knots or sutures are then employed to prevent upward displacement of the silastic tubing with respect to the cuff and to prevent downward displacement of the cuff with respect to the tubing.

Although fixation of the silastic tubing in the nasolacrimal system is a problem, the most troublesome problem is that scar tissue forms around the tubing thereby resulting in an obstruction which prevents tears from passing downwardly through the system around the exterior of the tubing.

In an effort to overcome the above-identified problems, applicant devised a catheter for use in the surgical correction of a nasolacrimal duct obstruction and the same was described in the co-pending application. Although the catheter of the co-pending application did satisfactorily perform in almost all cases, it has been found that the catheter sometimes migrates upwardly into the nasolacrimal sac. It has been found that such upwardly migration can be eliminated and the catheter immobilized by providing an enlarged portion at the lower end of the shank of the catheter.

It is therefore a principal object of the invention to provide a catheter for use with silastic tubing used in correcting nasolacrimal duct obstruction.

A further object of the invention is to provide a catheter of the type described which includes large portions at the upper and lower ends thereof to stabilize or immobilize the catheter.

Yet another object of the invention is to provide a catheter for use in the procedure described including enlarged portions at the upper and lower ends thereof which prevent longitudinal displacement of the catheter and the silastic tubing extending therethrough which can be left in vitro for two to six months without significant discomfort.

Yet another object of the invention is to provide a catheter for use in the described surgical procedure including enlarged portions at the upper and lower ends thereof which may be easily compressed to facilitate the postoperative removal thereof.

These and other objects of the present invention will be apparent to those skilled in the art.

SUMMARY OF THE INVENTION

A catheter is described for use with flexible silastic tubing having the ends thereof extended downwardly through the puncta, canaliculi, nasolacrimal sac and surgical bony opening onto the nose of a person's nasolacrimal system. The catheter has an internal diameter sufficient such that the free ends of the silastic tubing may be extended downwardly therethrough. The catheter has an enlarged head portion provided thereon at its upper end which is positioned in the nasolacrimal sac to prevent downward longitudinal displacement of the catheter as well as the silastic tubing. The catheter is also provided with an enlarged portion at its lower end which prevents upward longitudinal displacement of the catheter as well as the silastic tubing. The flexible characteristic of the enlarged head portion and enlarged portion at the lower end of the catheter permits the catheter to be easily removed postoperatively without excessive trauma. The method of using the catheter is also described.

DESCRIPTION OF THE PREFERRED EMBODIMENT

Figure 1:
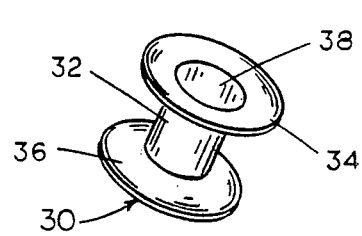
FIG. 1 is a perspective view of the catheter of this invention.
Figure 2:
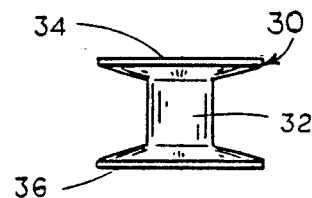
FIG. 2 is a side view of the catheter of FIG. 1.
Figure 3:
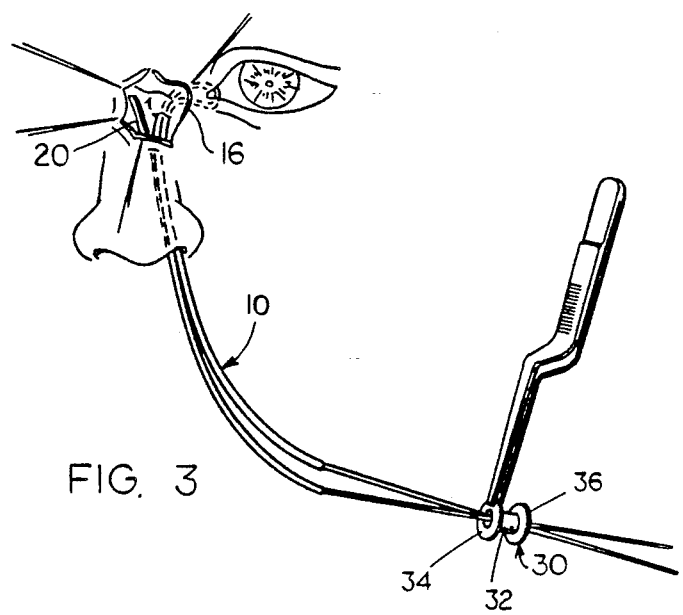
FIG. 3 is a perspective view illustrating the catheter of this invention being surgically positioned.
Figure 4:
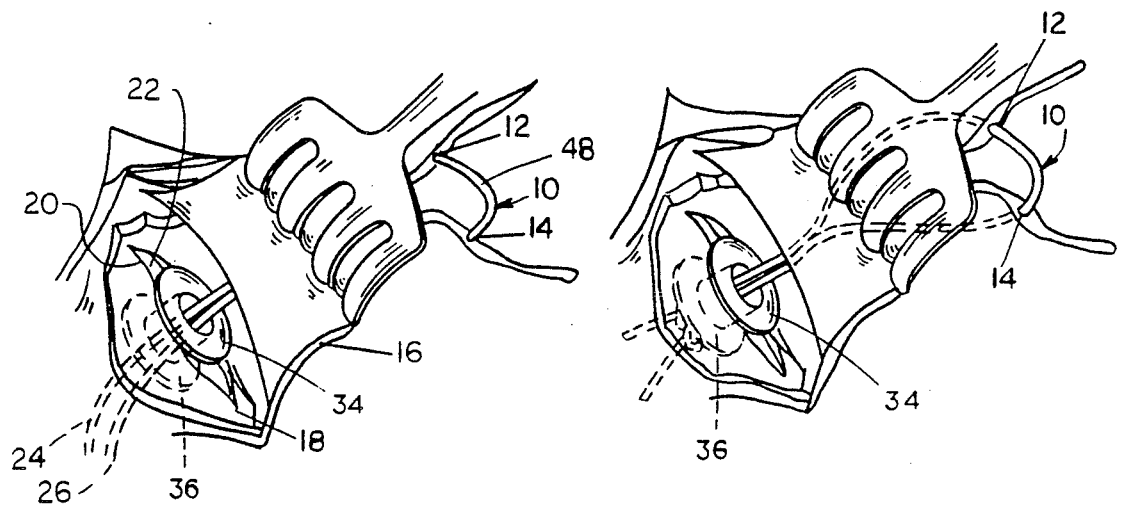
FIG. 4 is a perspective view illustrating the manner in which silastic tubing is extended downwardly through the puncta, canaliculi, into the nasolacrimal sac and outwardly through an incision created during a DCR procedure.
Figure 5:
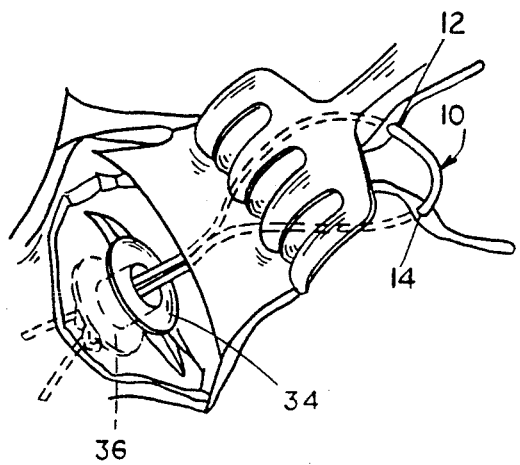
FIG. 5 is a view similar to FIG. 4 except that the catheter of this invention has been positioned in the nasolacrimal sac and the nasal cavity.

Referring to FIGS. 4 and 5, the numeral 10 refers to silastic tubing, the free ends of which are inserted downwardly through punctums 12 and 14 into the canaliculi communicating therewith. A conventional dacryocystorhinostomy procedure or technique (DCR) is performed by creating an incision 16 which communicates with the nasolacrimal sac 18. An incision 20 is also created to expose the nasal cavity 22. During the initial intubation procedure, the free ends 24 and 26 of the silastic tubing 10 are extended downwardly through the incision 20 as seen in FIG. 3 so that the free ends protrude from the patient's nostril.

The numeral 30 refers to the catheter of this invention which is preferably comprised of an inert material such as silastic or some similar alloplastic material such as "C-Flex". Catheter 30 includes a shank portion 32 having a preferred length of 7 millimeters. An enlarged upper end portion 34 is provided on the upper end of shank 32 and preferably has a diameter of approximately 15 millimeters. Similarly, an enlarged portion 36 is provided at the lower end of shank portion 32 and also preferably has a diameter of 15 millimeters. When necessary, the diameters of enlarged portions 34 and 36 may be trimmed to reduce the size thereof for better patient fit. An opening 38 is provided in the catheter for receiving the silastic tubing 10 as illustrated in the drawings. Preferably, opening 38 has a diameter of approximately 2 millimeters. Preferably, the enlarged portions 34 and 36 have a thickness of 0.5 millimeters.

When the silastic tubing has been positioned as previously described and as illustrated in FIG. 3, catheter 30 is slipped onto the free ends 24 and 26 of tubing 10 so that the ends 24 and 26 pass through opening or lumen 38 and downwardly through the catheter 30. The catheter 30 is then slipped upwardly on the tubing 10 as illustrated in FIG. 3 until the catheter is positioned as illustrated in FIGS. 4 and 5. A plurality of knots are also preferably formed in the tubing 10 below the lower end of the catheter 30 to prevent upward displacement of the tubing 10 with respect to the catheter 30 and to aid in preventing the downward displacement of the catheter 30 with respect to the tubing 10. As seen in FIG. 5, when the catheter 30 is in position, the enlarged portion 34 thereof is positioned in the nasolacrimal sac 18 and occupies a large portion thereof. The enlarged portion 34 prevents the catheter and the silastic tubing from being pulled upwardly into the canaliculi should the patient grasp the loop generally referred to by the reference numeral 48. The enlarged portion 36 is positioned in the nasal cavity below the incision 22 and also aids in preventing the catheter and the silastic tubing from being pulled upwardly into the canaliculi should the patient grasp the loop 48. Further, the enlarged portion 36 prevents the catheter from upward migration during the time that the catheter is in vitro. The catheter 30 functions substantially identical to the catheter of the co-pending application except that the enlarged portion 36 further aids in immobilizing the catheter.

The catheter 30 not only aids in fixing the silastic tubing but it also aids in maintaining a flow path for the tears through the nasolacrimal duct. The enlarged portion at the upper end of the catheter prevents the "scarring over" of the upper end of the nasolacrimal duct thereby preventing an obstruction from being formed which would interfere with the flow of tears.

After the catheter has been positioned as illustrated in FIG. 5, the DCR procedure would be completed with the incision then being closed. After a prescribed length of time, the silastic tubing 10 will be removed. The silastic tubing 10 is removed through the use of standard procedures with the loop 48 first being cut. The flexible enlarged portion 34 of the catheter 30 will easily deflect to permit the catheter to be pulled downwardly through the nasolacrimal duct when it is desired to remove the silastic tubing 10.

It is important to note that the enlarged portion 34 of the catheter also permits the shank portion 32 of the catheter to be quite short so that it will not objectionably protrude into the patient's nostril.

Thus it can be seen that the invention accomplishes at least all of its stated objectives.

I claim:
1. In combination,
   a flexible tube having its ends extended downwardly, through the puncta, canaliculi, nasolacrimal sac and nasal cavity of a person's nasolacrimal system,
   a catheter having upper and lower ends,
   the inside diameter of said catheter being such that the free ends of the flexible tube may be extended therethrough,
   the length of said catheter being such that said catheter may be extended into the upper end of the nasal cavity with the upper end thereof positioned in the nasolacrimal sac,
   said catheter having a flexible, enlarged head portion provided on its upper end for positioning in the nasolacrimal sac;
   said catheter having a flexible, enlarged portion provided on its lower end for positioning in the nasal cavity.
2. The combination of claim 1 wherein said flexible, enlarged head portion comprises a substantially flat disc-shaped member.
3. The combination of claim 2 wherein said enlarged portion at the lower end of said catheter comprising a substantially flat disc-shaped member.

* * * * *